United States Patent
Douaire et al.

(10) Patent No.: US 6,767,567 B1
(45) Date of Patent: Jul. 27, 2004

(54) INGESTIBLE ELEMENTS

(76) Inventors: Philippe Douaire, 12, Rue des Deux Ponts 75004, Paris (FR); Sandrine Vincensini, 1, Rue Corbineau 75012, Paris (FR)

( * ) Notice: Subject to any disclaimer, the term of this patent is extended or adjusted under 35 U.S.C. 154(b) by 0 days.

(21) Appl. No.: 09/720,569

(22) PCT Filed: Jun. 22, 1999

(86) PCT No.: PCT/FR99/01489
§ 371 (c)(1),
(2), (4) Date: Feb. 22, 2001

(87) PCT Pub. No.: WO99/66905
PCT Pub. Date: Dec. 29, 1999

(30) Foreign Application Priority Data

Jun. 22, 1998 (FR) .............................. 98 07838

(51) Int. Cl.[7] .............................. A23G 3/00; A61K 9/48
(52) U.S. Cl. .................. 426/75; 424/441; 424/451; 424/463; 424/467; 424/474; 426/89; 426/103; 426/104; 426/143; 426/660
(58) Field of Search .......................... 426/75, 89, 103, 426/104, 143, 660; 424/441, 451, 463, 467, 474

(56) References Cited

FOREIGN PATENT DOCUMENTS

| DE | 4342146 C1 | 7/1995 |
|---|---|---|
| EP | 0 214834 | 3/1987 |
| EP | 0 259219 | 3/1988 |
| FR | 2137872 | 12/1972 |
| FR | 2441341 | * 7/1980 .................. 426/75 |

OTHER PUBLICATIONS

J. P. Cleave; *Some geometrical considerations concerning the design of tablets; J. Pharm. Pharmacol.*; 1965; pp. 698–702; vol. 17; BNSDOCID; XP002096313.

P.H. List, et al.; *Hagers Handbuch der Pharmazeutischen Praxis; Springer Verlag;* 1971; p. 691; Figure 388A; Exemple Q; XP002096314; Berlin Heidelberg/New York.

Maria Edvige Sangalli, Paolo Giunechedi, Lauretta Maggi, Ubaldo Conte, Andrea Gazzaniga; *Inert Monolithic Device with a Central Hole for Constant Drug Release; European Journal of Pharmaceutics and Biopharmaceutics*; Dec. 1994; pp. 370–373; vol. 40, No. 6; XP000480157; Stuttgart, Germany.

* cited by examiner

*Primary Examiner*—Arthur L. Corbin
(74) *Attorney, Agent, or Firm*—Alston & Bird LLP

(57) ABSTRACT

The invention relates mainly to an element suitable for being ingested, the element including at least one air-passing channel making it possible to avoid choking in the event of being swallowed the wrong way. The present invention applies to the food industry and also to the pharmaceuticals industry.

6 Claims, 1 Drawing Sheet

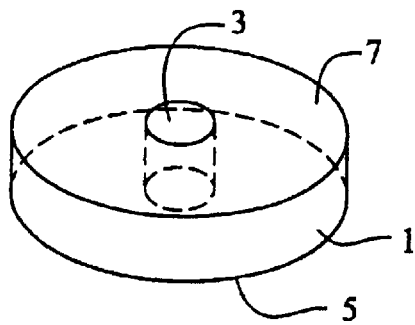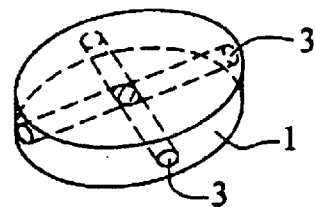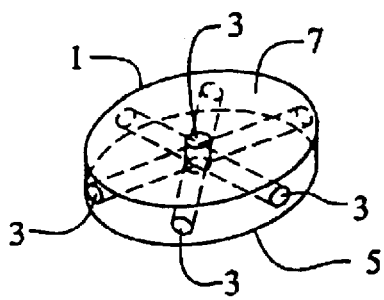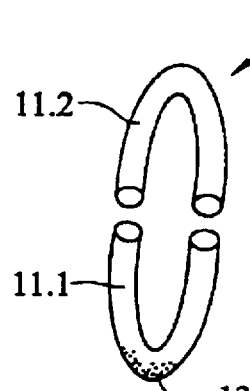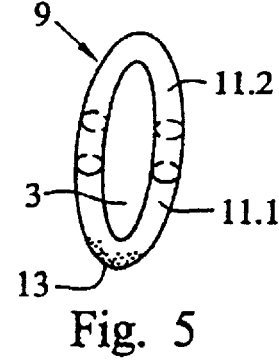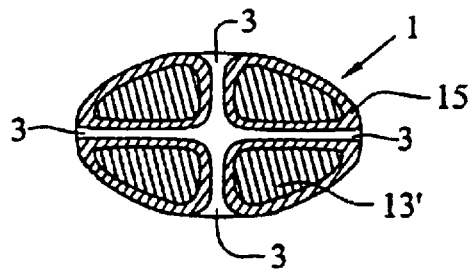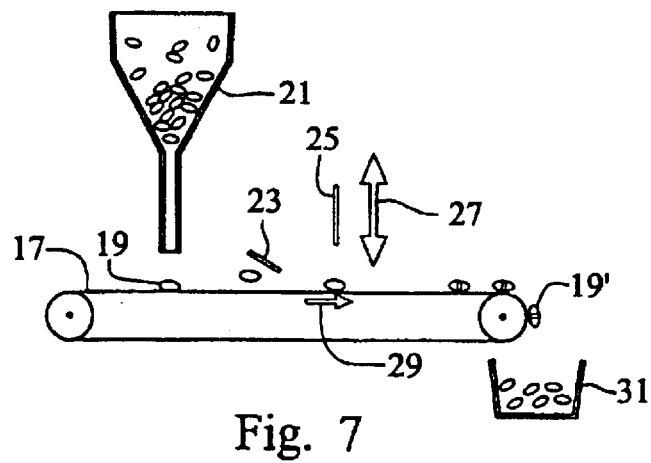

INGESTIBLE ELEMENTS

BACKGROUND OF THE INVENTION

The present invention relates mainly to elements that can be ingested such as sweets, candies, dried fruit, peanuts, or medicines to be taken orally.

Medicines, such as tablets, pills, or capsules, for example, and also certain foodstuffs such as, for example, nuts, sweets, candies, ice cubes, sugar lumps, confectionery, and chocolates are presented in the form of a relatively hard solid piece which, when swallowed the wrong way, in particular by an old person or by a child, and in particular a young child, runs the risk of blocking the airways, giving rise to choking.

SUMMARY OF THE INVENTION

Consequently, an object of the present invention is to provide ingestible elements that do not present a risk of choking when they are swallowed the wrong way.

Another object of the present invention is to provide such ingestible pieces of a shape that makes them easier to swallow.

Another object of the present invention is to provide medicines presenting active principle release properties that are optimized as a function of the prescribed treatment.

According to the present invention, these objects are achieved by an element of the medicine, sweet, candy, nut, dry charcuterie, or cheese type or the like in which at least one air flow channel is formed.

DESCRIPTION OF THE INVENTION

The invention will be better understood from the following description and the accompanying figures given as non-limiting examples, and in which:

FIG. 1 is a perspective view of a first embodiment of a tablet in accordance with the present invention;

FIG. 2 is a perspective view of a second embodiment of a tablet in accordance with the present invention;

FIG. 3 is a perspective view of a preferred embodiment of a tablet in accordance with the present invention;

FIG. 4 is a perspective view of a preferred embodiment of a capsule in accordance with the present invention prior to being assembled;

FIG. 5 is an analogous view of the FIG. 4 capsule after it has been assembled;

FIG. 6 is a section view of a coated tablet in accordance with the present invention; and FIG. 7 is a side view of a line for making air flow channels through ingestible elements in accordance with the present invention.

DETAILED DESCRIPTION OF THE INVENTION

In FIGS. 1 to 7, the same references are used to designate the same elements.

FIG. 1 shows a tablet 1 containing an active principle, such as aspirin for example, having a channel 3 made through the thickness thereof to interconnect the two main faces 5 and 7 of the tablet. The channel 3 allows air to flow through. Thus, if the tablet 1 should become stuck in a position where it blocks the trachea, the channel 3 allows air to pass through and avoids choking while waiting for the tablet to be evacuated from the airways. By way of example, the channel 3 can be cylindrical with a diameter lying in the range 0.5 mm to 6 mm, for example, preferably in the range 2 mm to 4 mm, e.g. equal to 2 mm, 3 mm, or 4 mm. Nevertheless, it should be understood that implementing channels having sections in the form of regular or other polygons, etc., and also channels of varying sections would not go beyond the ambit of the present invention.

FIG. 2 shows a tablet 1 in accordance with the present invention having a plurality of channels 3 distributed around its periphery and advantageously interconnected, e.g. at the center of the tablet. The tablet of FIG. 3 is chunkier in shape making it easier to swallow and it is also provided with channels 3 regularly distributed around its periphery plus a channel 3 interconnecting its main faces 5 and 7. All the channels are interconnected in the center of the tablet 1. Thus, whatever position the tablet might occupy if stuck in the trachea, the lungs remain connected via an air flow channel to the external medium containing air.

FIGS. 4 and 5 show a capsule 9 whose outer skin is constituted by a first U-tube 11.1 having an outside diameter substantially equal to the inside diameter of a second U-tube 11.2. The tubes are suitable for being engaged one in the other so as to form a tube in the form of a closed loop suitable for receiving microencapsulated particles of the activated principles of the medicine. The space between the walls of the tube forms an air-passing channel 3. The capsule 9 can be substantially toroidal, or on the contrary it can be flattened. In a variant, each of the tubes 11.1 and 11.2 is of varying diameter so that the outside diameter of the tapering end of a first tube corresponds to the inside diameter of the flared end of the other tube, thus enabling the tubes to be engaged in each other.

In a variant, the outer skin of the capsule is constituted by a single tube whose ends are engaged one in the other.

FIG. 6 shows an example of a coated tablet 1 in accordance with the present invention comprising an active principle 13' covered by a film 15 for preventing contact with the taste buds (for a medicine of disagreeable taste) or for controlling release of the active principle. By way of example, the film 15 can be based on sugar. Advantageously, the film 15 covers the active principle 13' completely, including inside the channels 3.

Naturally, the present invention is not limited to medicines but also applies to foodstuffs such as, for example, sweets, candies, biscuits, nuts, dry charcuterie, pieces of cheese, ice cubes, sugar lumps, confectionery, chocolates, and extruded products of the type comprising cocktail nibbles and the like. The elements can be obtained by compression or molding in molds having inserts corresponding to the channels 3. These inserts can be implemented, for example, in the form of rods that are fixed, or moving if that should be necessary to enable unmolding.

For foodstuffs that are not shaped in this way such as hazelnuts, peanuts, cashew nuts, or the like, the channels 3 are advantageously made by removing material mechanically or thermally. Material is advantageously removed by means of a punch, although drilling, mechanical machining, or laser machining would not go beyond the ambit of the present invention.

FIG. 7 shows a line for making channels 3 by removing material, advantageously by means of a punch. The line comprises a conveyor 17 fed with ingestible elements 19 by a feeder 21, e.g. a hopper. A mechanical guide device represented by 23 serves to orient the elements 19, in particular hazelnuts, peanuts, or advantageously, peanut halves.

The elements in which channels 3 are to be made come under a punch 25 (or other removal tool) driven with motion represented by arrow 27 perpendicularly to the travel direction 29 of the conveyor 17 and synchronized therewith. In a first embodiment, the conveyor 17 moves continuously and the punch 25 acts on moving targets. In a variant, the conveyor brings an element 19 under the punch 25 and then stops while the punch operates. The movement of the conveyor 17 then restarts and elements 19 with channels 3 are collected in a receptacle 31 for packaging.

The present invention applies to the food industry and also to the pharmaceuticals industry.

What is claimed is:

1. An ingestible element suitable for being ingested by a person, comprising a solid piece having first and second spaced apart, generally opposed main surfaces and a peripheral surface adjoining and interconnecting said first and second main surfaces, and at least two intersecting bores extending through said solid piece between said opposed main surfaces, each bore extending from one portion of said peripheral surface to another portion of the peripheral surface, and each bore defining at least one air-passing channel making it possible to avoid choking in the event of being swallowed the wrong way.

2. An element according to claim 1, wherein the channel is cylindrical or substantially cylindrical.

3. An element according to claim 2, wherein the channel has a diameter lying in the range 0.5 mm to 6 mm.

4. An element according to claim 1, wherein said element is a foodstuff.

5. An element according to claim 1, including an additional bore extending through the solid piece from said first main surface to said second main surface and intersecting said at least two intersecting bores to thereby provide a plurality of air flow channels.

6. An element according to claim 1, wherein said element is a tablet in the shape of a cylindrical disc having generally circular first and second main surfaces and an annular peripheral surfaces, and wherein each bore extends diametrically through said disc from a first position on said peripheral surface to a diametrically opposite position on said peripheral surface.

* * * * *